United States Patent [19]

Kobe

[11] Patent Number: 4,582,223

[45] Date of Patent: Apr. 15, 1986

[54] SYRUP SUPPLY METHOD AND APPARATUS FOR A POST-MIX BEVERAGE DISPENSER

[75] Inventor: Susumu Kobe, Tokyo, Japan

[73] Assignee: The Coca-Cola Company, Atlanta, Ga.

[21] Appl. No.: 500,432

[22] Filed: Jun. 2, 1983

[30] Foreign Application Priority Data

Aug. 2, 1982 [JP] Japan ................................ 57-133836

[51] Int. Cl.[4] ........................ B67B 7/24; B65D 47/10; A61M 37/00

[52] U.S. Cl. ........................................ 222/82; 222/91; 222/395; 222/541; 604/148; 604/411

[58] Field of Search ........................ 222/81, 82, 83, 89, 222/91, 395, 394, 541, 129.1; 604/140, 146, 147, 148, 201, 244, 411, 414

[56] References Cited

U.S. PATENT DOCUMENTS

| | | | |
|---|---|---|---|
| 1,995,098 | 3/1935 | Healy | 222/89 |
| 2,158,347 | 5/1939 | Yirava | 222/89 |
| 2,727,667 | 12/1955 | Booth | 222/129.1 |
| 3,186,577 | 6/1965 | Tennison | 220/244 |
| 3,208,639 | 9/1965 | Marwell et al. | 222/82 |
| 3,220,334 | 11/1965 | Martin | 222/395 |
| 3,424,346 | 1/1969 | Fruehling . | |
| 3,735,898 | 5/1973 | Smith | 222/395 |
| 3,783,895 | 1/1974 | Weichselbaum | 222/83 |
| 3,990,608 | 11/1976 | Walters . | |
| 4,216,885 | 8/1980 | Sedam | 222/481 |
| 4,281,775 | 8/1981 | Turner | 222/394 |
| 4,286,636 | 9/1981 | Credle | 141/114 |
| 4,296,786 | 10/1981 | Brignola | 222/83.5 |
| 4,306,667 | 12/1981 | Sedam . | |
| 4,356,937 | 12/1982 | Simon et al. | 222/81 |
| 4,359,432 | 11/1982 | Sedam et al. | 261/26 |
| 4,426,019 | 1/1984 | Sedam . | |
| 4,475,914 | 10/1984 | Portnoff | 222/83 |

FOREIGN PATENT DOCUMENTS

| | | | |
|---|---|---|---|
| 1232980 | 10/1960 | France . | |
| 1316658 | 12/1961 | France | 222/81 |

*Primary Examiner*—Joseph J. Rolla
*Assistant Examiner*—Andrew Jones
*Attorney, Agent, or Firm*—Birch, Stewart, Kolasch & Birch

[57] ABSTRACT

An apparatus and method for connecting a one-way disposable syrup package and associated dispensing attachment for use in a post-mix beverage dispenser system are described. The dispensing attachment includes a threaded socket for operatively engaging the threaded portion on the neck of a container constituting the syrup package, a cutting edge for puncturing a sealing member over the discharge end of the container, an inlet for supplying a compressed fluid into the container and an outlet for propelling the syrup concentrate toward the discharge opening of the container. The dispensing attachment is screwed onto the threaded portion of the container neck, preferably while the container is in an upright position until the cutting edge punctures the sealing member. Suitable conduits are then connected to the inlet and outlets of the attachment to connect the syrup package to the post-mix beverage dispenser system.

5 Claims, 2 Drawing Figures

SYRUP SUPPLY METHOD AND APPARATUS FOR A POST-MIX BEVERAGE DISPENSER

BACKGROUND OF THE INVENTION

The present invention relates to a method for the conveying and mixing of syrup concentrate in a post-mix beverage dispenser and an apparatus for use in such method.

Post-mix beverage dispensers are known for mixing syrup concentrate, i.e., a concentrate such as cola, juice or the like, soda water and/or water with ice in a cup.

The conveying of syrup concentrate within such devices has been accomplished using various forms of syrup containers with associated connectors fastened thereto. Examples of such containers are the well-known steel containers commonly known as FIGAL containers, such as disclosed in U.S. Pat. No. 3,186,577 to Tennison.

Syrup concentrate for post-mix beverage dispensers is generally loaded into these FIGAL containers at syrup production plants, shipped to the point of use in post-mix beverage dispensers, and returned to the factory for refilling and reuse. However, with such two-way syrup containers, it is necessary to store large numbers of syrup containers, convey, collect, wash and inspect them adequately in order that containers filled with syrup concentrate may be used with good efficiency. The management of large numbers of such syrup containers has become very complicated and difficult because of an increasing number of syrup containers required.

To provide alternatives to the use of two-way syrup containers, such as steel FIGAL containers, systems have been designed heretofore using one-way disposable syrup packages such as in the gravity feed systems of U.S. Pat. Nos. 4,216,885 and 4,359,432 to Sedam, et al. and the bag-in-box system of U.S. Pat. No. 4,286,636 to Credle, all of which are assigned to the same assignee as the present invention.

The present invention provides a further alternative to the use of two-way refillable syrup containers in post-mix beverage dispenser systems.

SUMMARY OF THE INVENTION

Accordingly, a primary object of the present invention is to provide a method for connecting a one-way, disposable syrup package and an associated dispensing attachment therefor into a post-mix beverage dispenser system or cup-type vending machine.

A further object of the present invention is to provide a dispensing attachment for a one-way syrup container which facilitates rapid and efficient connection of a syrup supply to post-mix beverage dispensers or cup-type vending machines.

The objects of the present invention are fulfilled by:

(a) providing a container with syrup concentrate therein, said container having a neck portion defining a discharge opening at one end thereof and having a threaded portion thereon, said discharge opening being covered by a sealing member;

(b) screwing a dispensing attachment onto the neck of said container, said dispensing attachment comprising a threaded socket for operatively engaging the threaded portion of the neck of said container, a cutting edge for puncturing said sealing member, an inlet for supplying a compressed fluid into the container and an outlet for propelling the syrup concentrate toward the discharge opening of said container;

(c) puncturing said sealing member with said cutting edge; and (d) transporting syrup concentrate to said mixing station in said post-mix beverage dispenser.

BRIEF DESCRIPTION OF THE DRAWINGS

The objects of the present invention and the attendant advantages thereof will become more readily apparent by reference to the following drawings wherein.

DETAILED DESCRIPTION OF INVENTION

Figure 1:
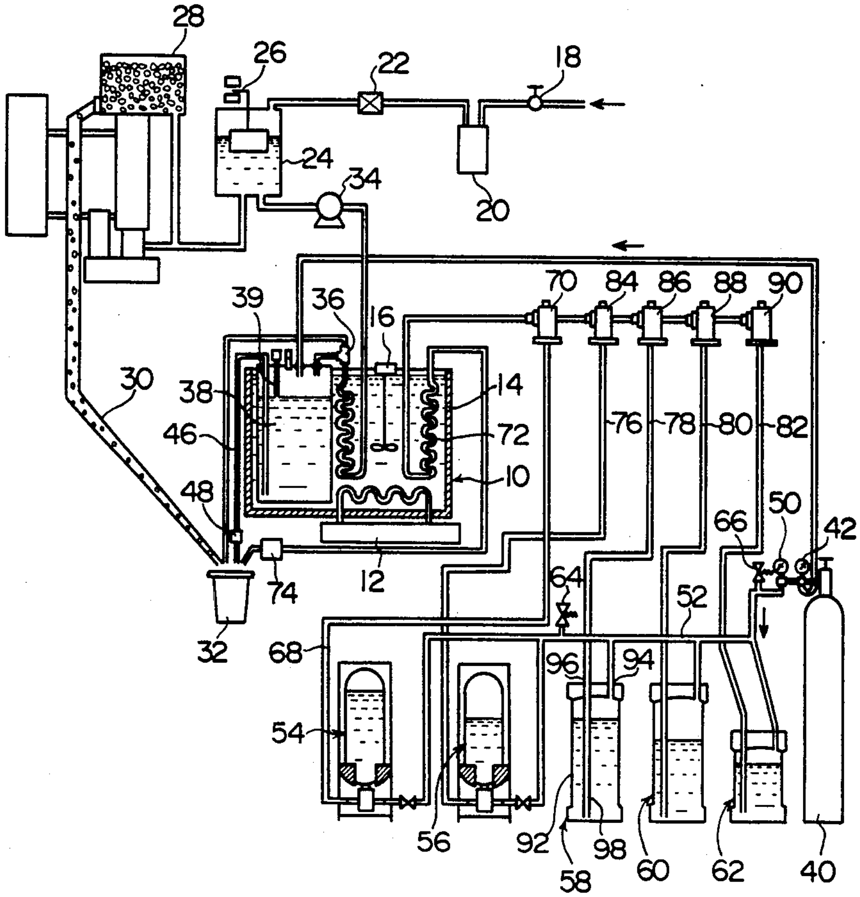
FIG. 1 is an exemplary post-mix beverage dispensing or cup vendor system in which the present invention may be implemented.

Referring to FIG. 1, there is illustrated an example of a cup vendor or post-mix beverage dispenser system which can be used for the method of conveying and mixing of syrup concentrate in accordance with the present invention.

In this vending machine of FIG. 1, a syrup concentrate, i.e., a concentrate such as cola or juice, soda water and/or water are to be mixed with ice in a cup and served to a customer. This vending machine includes a cooling apparatus 10 for cooling syrup concentrate, soda water and water. The cooling apparatus 10 comprises a refrigerator 12, a water bath 14 and an agitator 16, whereby water in the water bath 14 is maintained at a temperature of about 1°–2° C.

Water for preparing ice and soda water is stored in a tank 24 from a general water service via a cock 18, a filter 20 and a valve 22. The water level in the tank 24 is kept constant by a water level detector 26 including a valve 22. Water is supplied to an ice maker 28 from the tank 24. The ice maker 28 is designed to supply a given amount of chip-like ice to a cup 32 via a conduit 30 in response to an electric signal. Further, the tank 24 may supply cooled water to the cup 32 via a pump 34, cooling apparatus 10 and an electromagnetic valve 36. This cooled water is used for preparing a juice, free from soda water, or water having a low carbonate concentrate. An electromagnetic valve 36 is provided to supply cooled water to the carbonator 38. Also fed to the carbonator 38 is $CO_2$ gas adjusted to a pressure of the order of 5 kg/cm$^2$ by a first pressure regulator 42 from a $CO_2$ gas cylinder 40. The quantity of a liquid in the carbonator 38 is designed to be maintained constant, automatically, by detecting a change in electric resistance between an electrode 39 and carbonator container 38. Further, the following construction is possible, i.e., a control system in which the weight of carbonator 38 is detected to thereby maintain its quantity of liquid constant. Soda water produced by the carbonator 38 is supplied to the cup 32 via conduit 46 and electromagnetic valve 48. The electromagnetic valve 48 has its opening and closing controlled by an electric signal.

$CO_2$ gas coming from the $CO_2$ gas cylinder 40, adjusted by a second pressure regulator 50 to be a pressure of the order of 3–3.5 kg/cm$^2$, is supplied to a plurality of syrup containers 54, 56, 58, 60 and 62 via a communicating vessel 52 (i.e., an inflow straight pipe). The communication vessel 52 is optionally equipped with safety valves 64, 66. The syrup pressurized in the syrup container 54 is supplied to the cup 32 via conduit 68 (i.e., an outflow conduit), flow regulator 70, conduit 72 extending within the cooling apparatus 10 and electromagnetic valve 74. The syrup in each of the syrup containers 56, 58, 60 and 62 is supplied to the cup 32 via conduits 76, 78, 80 and 82, flow regulators 84, 86, 88 and 90 and a conduit extending within the cooling apparatus 10 and electromagnetic valve, both not shown in the drawing.

The cup vendor or post-mix beverage dispenser of FIG. 1 will operate essentially as follows:

The display surface of the vendor (not shown) has a plurality of push-buttons, each connected to an electric switch. If one inserts a coin and presses one of these push-buttons, an electric switch connected to such button is closed. An electric signal generated by this causes a given amount of ice to be supplied to the cup 32 from the ice maker 28. Further, an electromagnetic valve 48 is opened for a fixed period of time, for example, with the result that a (predetermined) quantity of soda water is supplied to the cup 32. Similarly, a valve 74 is opened for a fixed period of time, and consequently, the syrup concentrate in the syrup container 54 is supplied to the cup 32 in any fixed amount, whereby an iced carbonated drink, e.g., cola is prepared and served to a customer. In the case of an uncarbonated drink, such as juice, ice and water are supplied through the electromagnetic valve 36 and a desired concentrated syrup are supplied to the cup 32. To prepare and serve a drink having a low carbonate concentration, both electromagnetic valves 36 and 48 are opened, whereby water and soda water are supplied into the cup in a predetermined amount.

In the method of the present invention for conveying and mixing syrup concentrate, a fully-automatic machine may also be employed. This fully-automatic machine is a device in which the concentrated syrup, soda water and/or water and, if desired, ice are supplied to the cup in predetermined proportions. Accordingly, to this device, an optional amount of Cola, juice or the like can be obtained depending on the push-button selection.

The supply of concentrated syrup to post-mix beverage dispensers has been conducted to a great extent heretofore using containers such as syrup containers 58, 60 and 62 in FIG. 1. These syrup containers include a cylindrical main body 92 of stainless steel. In the upper part of this main body 92 are disposed two one-way valves 94 and 96. Through one of these one-way valves 94 is supplied pressurized $CO_2$ gas. To the other one-way valve 96 a tube 98 is connected. This tube 98 extends to the base of the main body 92. The one-way valve 96 is connected to a flow regulator 86 via a connector equipped with non-return release means and conduit 78. These syrup containers 58, 60, 62 are filled with syrup concentrate in a syrup supply station such as syrup production factory, and the so-filled containers are conveyed to a post-mix beverage dispenser where syrup concentrate is supplied from the containers. Thereafter, syrup containers 58, 60, 62 are collected for reuse. Containers of this type are commonly called FIGAL containers, such as disclosed in U.S. Pat. No. 3,186,577 to Tennison.

Figure 2:
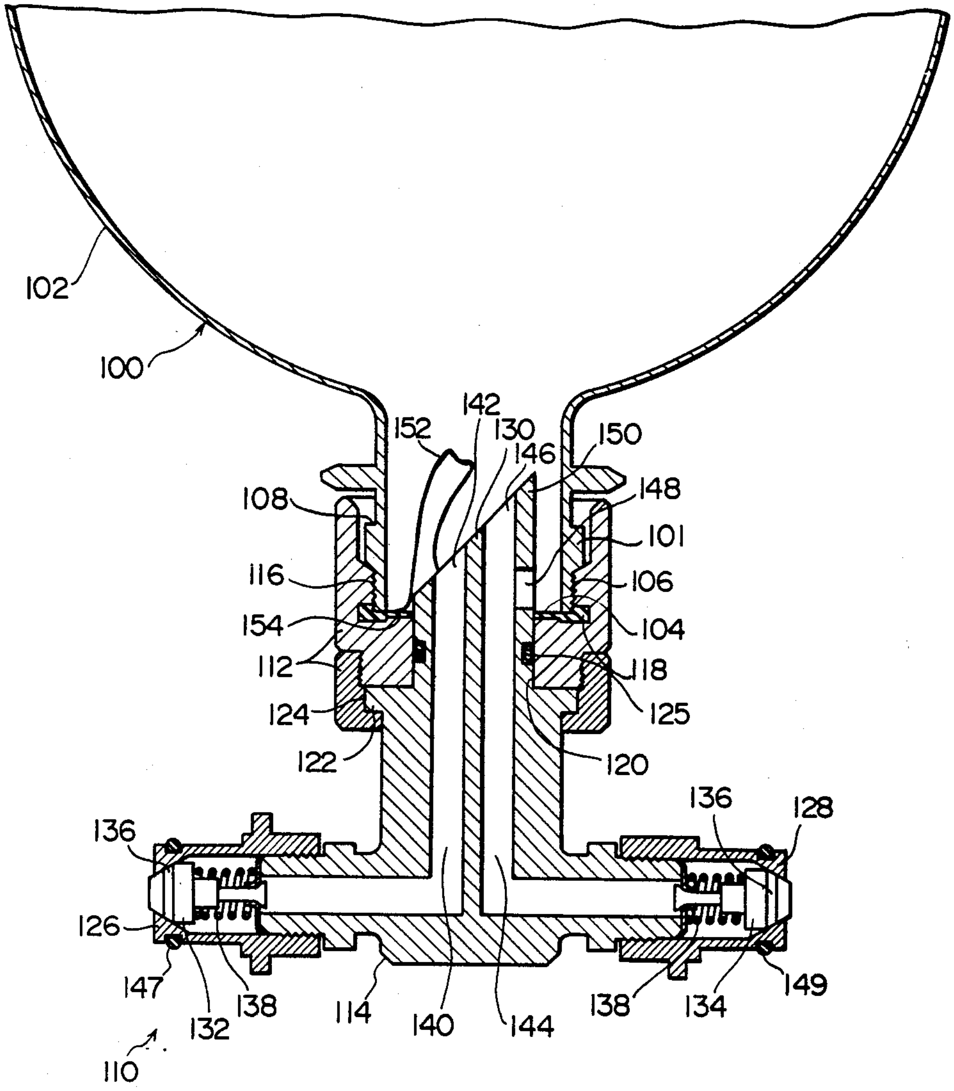
FIG. 2 is a partial view in section of a one-way syrup package connected to an associated dispenser attachment of the present invention for use in the system of FIG. 1.

The method for conveying and mixing syrup concentrate according to the present invention and a dispensing attachment for use in such method may be understood by referring to FIGS. 1 and 2 together.

In accordance with the above method of the present invention, syrup concentrate is first filled in a syrup container 100 (FIG. 2) at a syrup supply station such as a syrup factory, etc. This container 100 has the same structure as those of the containers 54, 56 indicated in FIG. 1. The container 100 is manufactured using pressure-resistant synthetic resins, such as PET (polyethylene terephthalate), PVC (Polyvinyl chloride resin), PE (polyethylene), PS (polystyrene), PP (polypropylene), PVPC (polyvinylidene chloride), etc. Production of the container 100 from PET (Polyethylene terephthalate) by blow molding is preferred. The container 100 has a neck 101 and a nearly cylindrical thin main body 102. The neck 101 has a threaded portion 106 into which a cap and dispenser attachment are screwed, as described hereinafter. The main body 102 is constructed to withstand a relatively high pressure exerted on the interior of the container 100. After filling syrup concentrate into the container 100 at the syrup supply station, an opening in the neck 101 of the container 100 is sealed with a sealing member 104. The sealing member 104 may be a thin film in the form of three layers including polyethylene, aluminum and PET. With PET inside, (the container side) this sealing member may be bonded to the end of the neck 101 of the container 100 by heating, for example. The thin film for sealing member 104 in the alternative can be used a three-layered film of aluminum (15μ), polyethylene (50μ) and a hot-melt (5–10μ) with the hot-melt inside. Further, a two-layered film of aluminum (15μ) and PET (50μ) with PET Inside can be also employed.

In order to protect the sealing member 104 during the conveying of containers from the factory, and prevent its contamination, a cap (not shown) is screwed onto a threaded portion 106 of the neck 101 of the container 100 after sealing with the sealing member 104.

For this cap, it is preferable to have an inside flange to make it pilfer-proof. This flange extends in the direction of a central axis of the neck 101 so that it engages with a shoulder 108 of the neck 101 of the container 100, together with a threaded portion of neck 101 screwed into the threaded portion 106.

The container 100 being filled with syrup concentrate, sealed with the sealing member and capped above is conveyed to post-mix beverage dispenser sites by a vehicle, for example. At this site, the following steps are performed: screwing of the dispenser attachment onto the neck 101 of the container 100, rupturing of the sealing member 104 and dispensing of the concentrate from the container 100 in the following manner.

After the cap is taken off, a dispensing attachment 110 is fastened to the container 100. A preferred embodiment of the dispensing attachment 110 is illustrated in FIG. 2. According to this embodiment, the dispensing attachment 110 has a threaded socket 112 and main body 114 rotatably connected thereto. After fastening the dispensing attachment 110 to the container 100, this attachment is used by inverting the container 100. Therefore, its inverted state is shown in FIG. 2.

The threaded socket 112 has a screw attached part 116. This part 116 is screwed onto the threaded portion 106 of container neck 101 after removing the cap from the neck 101 of the container 100, whereby the attachment 110 becomes fastened to the container 100. At the inner base of the threaded socket 112 is disposed a gasket 118. When the screw attached part 116 of the threaded socket 112 is screwed onto the threaded portion 106 of the container 100, this brings the threaded socket 112 and the container 100 into full engagement with each other. The screw attached part 116 has a central hole 120. In this hole 120 is rotatably positioned the main body 114 of the dispensing attachment. As illustrated, the main body 114 has a circular flange 122. In the central hole 120 of the screwed attached portion 116 is formed a circular recess 124 housing this flange 122. This allows the main body 114 to rotate in the central hole 120 of the screwed attached portion 116 with its center axis (vertical direction in FIG. 2) as a focal point. However, its movement along the central axis is restricted. Further, an O-ring 125 is positioned between the main body 114 of the dispensing attachment and screwed portion 112, thereby maintaining a seal therebetween. In order that the circular flange 122 of the main body 114 may be easily housed within the circular recess 124 of the hole 120 of the screw attached portion 116, it is preferable that the threaded socket 112 include a separate screw attached part 116, as shown in FIG. 2.

The main body 114 of the dispensing attachment has an inlet port 126, outlet port 128 and insertion port 130. The inlet port 126 and outlet port 128 are provided with one-way check valves 132 and 134, respectively. These check valves 132 and 134 are optionally of the structure as generally known. For instance, they have a valve body 136 and a spring 138 forcing the body 136 outwardly. By virtue of this, these check valves 132 and 134 are usually closed, but their exterior and interior are caused to communicate with each other when the exterior has a sufficiently high pressure over the interior. An inlet conduit 140 extends from the check valve 132 of the inlet port 126 to the insertion part 130 and opens at an inlet opening 142 in the insertion part 130. Accordingly, when the dispensing attachment 110 is fully fastened to the container 100 and the check valve 132 is open, the inlet passage 140 causes the container 100 to communicate its interior and exterior with each other. Similarly, an outlet passage 144 extends from the check valve 134 of the outlet port 128 to the insertion part 130. The outlet passage 144 opens at two outlet openings 146 and 148 in the insertion part 130. Surrounding the inlet port 126 and the outlet port 128 are O-rings 147 and 149, respectively, in order that suitable conduits may be attached thereto. Accordingly, if an inlet conduit is connected to the port from a $CO_2$ gas cylinder, and if pressurized $CO_2$ gas is supplied, this $CO_2$ gas will be supplied via the inlet conduit, check valve 132, inlet passage 140 and inlet opening 132. The outlet side of an outlet conduit is connected to the outlet port 128 by a quick-disconnect coupling having a convex portion which presses the valve body 136 inwardly against the spring 138.

The insertion part 130 of the main body 114 of the attachment is provided with a cutting edge 150 for severing the sealing member 104 which seals the opening of the container 100.

As shown in FIG. 2, the nearly cylindrical insertion part 130 can be made into a shape as if it were cut by one slope, and its end can be terminated in a cutting edge 150. The shape of the cutting edge 150 is not restricted as shown, but may vary.

Fixing the dispensing attachment 110 according to the preferred embodiment indicated in FIG. 2 to the container 100 is conducted in the following way. Firstly, the conveyed container 100 is placed on the floor in a normal condition, i.e., with the neck 101 upward. Then the cap is removed and the attachment 110 is aligned with the neck 101, to thereby push down the attachment 110, whereby the cutting part 150 of the attachment 110 partially severs the sealing member 104. Next, the screw attached part 116 of the attachment 110 is screwed onto the threaded portion 106 of the container 100. By the termination of this screwing, the fixing is completed. Even after completion of the fixing, a cut portion 152 of the sealing member 104 is severed by the cutting edge 150, but is not usually completely separated. That is, the cut portion 152 becomes flap-like, as fully described below.

Such a construction is proposed that the screwing between the screw attached part 116 and threaded portion 106 and severance of the sealing member 104 by the cutting edge 150 may have the following relationship. Namely, the attachment 110 is firstly pressed against the neck of the container 100 by alignment, thereby to rotate the threaded socket 112 of the attachment 110 several times, whereby the screw attached part 116 and threaded portion 106 are partially screwed into each other. In this state, the cutting part 150 is so designed that it has not yet cut the sealant 104. Such a construction becomes possible by positioning the cutting edge 150, screw attached part 116 and threaded portion 106 adequately. Next, the threaded socket 112 is further rotated to thereby cause the cutting edge 150 to advance side-by-side along its axial direction and cut the sealing member 104. By the completion of screwing the screw member 116 into the threaded portion 106, the attachment 110 is completely fastened to the container 100. This construction is especially preferred for sanitary reasons in that by the partial screwing between the screw attached part 116 and threaded portion 106, the communication of the external atmosphere with the interior is generally interrupted and then the sealing member is severed.

Further, a construction is also proposed such that after completion of the screwing between the screw attached part 116 and threaded portion 106, the sealing member is severed by the cutting edge 150. That is, firstly the threaded socket 112 of the attachment 110 is made into a structure which is relatively long in its axial direction (the vertical direction in FIG. 2). The circular recess 124 is removed. The main body 114 of the attachment is also made into a structure which is comparatively long in its axial direction. The circular flange 122 is removed. Such construction enables the main body 114 to move axially (the vertical direction in FIG. 2) with respect to the screwed portion 112. The O-ring 125 is disposed as such, and in the course of movement of its axial direction, the sealing between the main body 114 and screwed portion 112 is maintained. Further, the device of the present invention is so constructed that the cutting edge 150 of the main body 114 is located between two positions, i.e., a position not projecting but recessed from the discharge opening 154 of the threaded socket 112, and a projected position from the discharge opening 154, as shown in FIG. 2. The main body 114 of the attachment and the threaded socket 112 are constructed in the above way, thereby to maintain the cutting edge 150 and accordingly the main body 114 of the attachment at the recessed position, whereby the screw attached part 116 of the screwed portion 112 is screwed into the threaded portion 106. By virtue of the above construction, the cutting edge 150 has not severed the sealing member 104 even after completion of this screwing. After completion of this screwing, the cutting edge 150 and therefore the main body 114 is moved to the projected position and then kept at this position. By this movement, the cutting edge 150 severs the sealing member 104.

The insertion part 130 of the main body 114 of the attachment will now be described in more detail. As above, the insertion part 130 has a cutting edge 150; an inlet opening 142 of the inlet passage 140; and outlet openings 146, 148 of the outlet passage 144. According to the preferred embodiment shown in FIG. 2, the cutting edge 150 is formed with a slope. If the insertion part 130 is inserted into the neck 101 of the container 100 in such a manner that they do not rotate relatively, the cutting of the sealing member 104 starts from the right side of FIG. 2. And during its insertion, the cutting position moves to the left side. Even after the completion of insertion of the insertion part 130, the severed portion 152 of the sealing member 104 is not completely separated from the remainder of the member. That is, in the right side of FIG. 2 the severed portion and the remainder are separated from each other and its right end becomes a free end. While in the left side the severed portion 152 and the remainder are connected to each other. Accordingly, the severed portion 152 forms a flap. This flap may become an obstacle to the discharge of concentrated syrup, as indicated below.

That is, assume that the device of this application is so constructed that as opposed to the example of FIG. 2, a fluid such as $CO_2$ gas is introduced from the outlet passage 142 and syrup concentrate is discharged from the inlet passage 142. In this case, the syrup concentrate is discharged via the inlet opening 142. The flap 152 is located in the area of the opening 142. Because of this, the flap, if it is constructed of a soft material, may clog the inlet opening 142. Consequently, the discharge of syrup concentrate is hindered.

Further, let it be supposed that the device of this application has been constructed as in the example of FIG. 2 but the outlet opening 148 is not provided. If the fluid is inflowing through the opening 142, the flap 152 does not become an obstacle to such inflow even on the assumption that it is positioned in the vicinity of the opening 142. Therefore, this poses no problem. Further, the concentrated syrup is discharged via the outflow opening 146 since the opening 146 is remote from the flap. Accordingly, this situation presents no problems. However, if a lower outflow opening 148 is not provided, this gives rise to such a new problem that all syrup concentrate cannot be discharged at the final stage of discharge from the container 100 of the syrup concentrate. That is, the provision of only the upper outflow opening 146 is unable to discharge the syrup concentrate left in the lower portion (FIG. 2) of the opening 146.

In the attachment 110 as illustrated in FIG. 2, the inlet opening 142 is arranged at the relatively low position of a slant face forming the cutting edge 150, whereby the flap 152 of the sealing member 104 is disposed in the area of this opening 142. However, the flap 152 does not become an obstacle, because this is not an outlet but an inlet. Further, the attachment 110 has the outlet opening 148 at a position remote from the flap and its position is low. Accordingly, the syrup concentrate can be discharged without obstruction by flap 152 in a nearly perfect manner. This being so, the provision of only the lower outflow opening 148 is sufficient. It is not always necessary to make an upper outflow opening 146.

Moreover, an explanation will now be made of the relationship between the flap 152 and outlet opening 148. The threaded socket 112 contacts face-to-face with the end of the neck 101 of the container 100 on the inside bottom wall via the sealing member by the screwing of the screw attached part 116 into the threaded portion 106. A portion projected from the above discharge opening 154 of the main body 114 becomes the insertion part 130 and this is inserted into the neck 101 of the container 100 through the sealing member. As shown in FIG. 2, when the insertion part 130 assumes a shape obtained when cutting a cylindrical body by a plane at an angle, its end becomes the cutting edge 150. The flap 152 of the sealing member 104 is left at the position opposite to the circumferential direction of the cutting edge 150 situated in the right side of FIG. 2, i.e., in the neighborhood of the left side of FIG. 2. The outflow opening 148 is aligned with the cutting edge 150 in the circumferential direction, and when it is disposed at a position adjacent the discharge opening 154, syrup concentrate can be discharged entirely without any obstruction by the flap 152.

Further, the syrup concentrate can be discharged entirely by arranging a plurality of communication ports connected to the outlet passage 144 in the region just above the discharging opening 154 or by providing within its vicinity a concave portion communicating to the outlet passage 144. In these cases, it is unnecessary to consider where the flap 152 is formed.

As described above, the container 100 conveyed to the dispensing site is provided with the above attachment 110 firstly in a normal position state. Thereafter, the container 100 is set in a dispenser, for example, a cup vendor as indicated in FIG. 1 in the inverted state, i.e., with the neck 101 downward. Further, after fastening the attachment 110 to the container 100, an inlet conduit and outlet conduit are attached to the inlet port 126 and outlet port 128 of the attachment 110, respectively. Or the following is done, i.e., after attaching the inlet conduit and outlet conduit to the inlet port 126 and outlet port 128 of the attachment 110, respectively, the attachment is fastened to the container. The container 100 is then supplied with pressurized $CO_2$ gas, for example, by opening the cock of the $CO_2$ gas cylinder. And as the electromagnetic valve 74 is opened, the syrup concentrate in the container is supplied into a container, such as a paper cup.

As described above, as a result of the container 100 being inverted at the time of syrup concentrate supply, the length of the insertion part 130 of the attachment 110 to be inserted into the neck 101 of the container 100 may be short. If the syrup concentrate is supplied with the container upright, the syrup must be discharged from the base of the container, whereby the attachment 110 would have to have a long tube.

In the above example, the $CO_2$ gas cylinder is connected to the inlet port 126 of the attachment 110 via the inlet conduit and the outlet conduit is connected to the outlet port 128. A modification of such an arrangement could use two containers 100 connected in series. That is, to the inlet port 126 of the first container 100 is connected the $CO_2$ gas cylinder via the inlet conduit. And the outlet port of the first container is connected to the inlet port of the second container by means of the conduit. And the outlet port of the second container is connected to the outlet conduit and the syrup concentrate is supplied to a cup via the outlet conduit and electromagnetic valve. Connecting them in this way makes it possible to place the syrup concentrate in twofold quantities in one set. In this case, the compressued fluid for discharging the concentrated syrup in the second container is the same as that in the first container.

It should be further understood that the post-mix beverage dispenser system described hereinafter may be further modified by one of ordinary skill in the art without departing from the spirit and scope of the present invention.

What is claimed is:

1. A post-mix beverage dispenser comprising:

(a) at least one syrup container, said container having a neck with a threaded portion and a discharge opening at one end thereof;

(b) a rupturable sealing member covering said discharge opening;

(c) an attachment for dispensing syrup from said container including, a threaded socket for operatively engaging the threaded portion on the neck of said container and fastening said attachment to said container in response to relative rotation of said socket and said neck, and a main body mounted within said threaded socket including a cylindrical central portion with a truncated end forming a cutting edge at a peak thereof, said cutting edge extending into the neck of said container through said rupturable sealing member when said attachment is fastened to said container, said cutting edge being so shaped and dimensioned as to form a movable flap in said sealing member overlying the entire said truncated end when said cutting edge extends through said sealing member, an inlet opening and an outlet opening in said truncated end, the other end of said central portion being connected to a base portion, and inlet and outlet ports in said base portion, and inlet and outlet passages connecting said inlet and outlet ports with the interior of said container through said inlet and outlet openings in said truncated end;

(d) a source of pressurized fluid connected to the inlet port in said base portion to thereby introduce the pressurized fluid through said inlet passage and the inlet opening in said truncated end to lift said movable flap off of the truncated end, said pressurized fluid also forcing said syrup out of the inlet opening in said truncated end, through said outlet passage and said outlet port.

2. The post-mix beverage dispenser of claim 1, wherein said container has the discharge opening at the bottom thereof and said central portion has an additional outlet opening disposed below said cutting edge contiguous to said sealing member, said additional outlet opening also communicating with said outlet passage and outlet port.

3. The post-mix beverage dispenser of claim 1, wherein the outlet opening in said truncated end is adjacent the peak thereof.

4. The post-mix beverage dispenser of claim 1, wherein the main body is rotatable within said threaded socket.

5. The post-mix beverage dispenser of claim 1, wherein the main body is axially movable with respect to said threaded socket.

* * * * *